United States Patent

Neuberger et al.

(10) Patent No.: US 8,425,495 B2
(45) Date of Patent: Apr. 23, 2013

(54) MULTIPURPOSE DIODE LASER SYSTEM FOR OPHTHALMIC LASER TREATMENTS

(75) Inventors: Wolfgang Neuberger, Labuan (MY); Detlev Berndt, Köln (DE); Julian Maughan, Salisbury (GB)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 1072 days.

(21) Appl. No.: 11/157,901

(22) Filed: Jun. 17, 2005

(65) Prior Publication Data

US 2005/0240168 A1 Oct. 27, 2005

Related U.S. Application Data

(63) Continuation-in-part of application No. 10/317,921, filed on Dec. 11, 2002, now abandoned.

(51) Int. Cl.
*A61B 18/20* (2006.01)

(52) U.S. Cl.
USPC .............................................. 606/4; 128/898

(58) Field of Classification Search ....... 606/4; 128/898
See application file for complete search history.

(56) References Cited

U.S. PATENT DOCUMENTS

| | | | |
|---|---|---|---|
| 4,143,941 A * | 3/1979 | Soref | 385/18 |
| 4,699,482 A * | 10/1987 | Utsugi | 351/206 |
| 4,917,486 A | 4/1990 | Raven et al. | |
| 5,144,630 A | 9/1992 | Lin | |
| 5,147,349 A * | 9/1992 | Johnson et al. | 606/4 |
| 5,268,920 A * | 12/1993 | Esterowitz et al. | 372/71 |
| 5,295,989 A | 3/1994 | Nakamura | |
| 5,331,649 A | 7/1994 | Dacquay et al. | |
| 5,423,798 A | 6/1995 | Crow | |
| 5,442,487 A * | 8/1995 | Mizuno | 359/784 |
| 5,461,692 A * | 10/1995 | Nagel | 385/127 |
| 5,892,569 A * | 4/1999 | Van de Velde | 351/221 |
| 6,059,772 A * | 5/2000 | Hsia et al. | 606/4 |
| 6,471,691 B1 * | 10/2002 | Kobayashi et al. | 606/4 |
| 6,532,244 B1 * | 3/2003 | Dewey et al. | 372/29.014 |
| 2001/0033595 A1 * | 10/2001 | Miyake | 372/66 |
| 2002/0001080 A1 * | 1/2002 | Miller et al. | 356/326 |
| 2003/0100824 A1 * | 5/2003 | Warren et al. | 600/407 |
| 2004/0078029 A1 * | 4/2004 | Momiuchi et al. | 606/4 |
| 2005/0055015 A1 * | 3/2005 | Buzawa | 606/4 |
| 2005/0254008 A1 * | 11/2005 | Ferguson et al. | 351/205 |

\* cited by examiner

*Primary Examiner* — Bill Thomson
*Assistant Examiner* — Jeffrey Lipitz
(74) *Attorney, Agent, or Firm* — BJ Associats; Bolesh J. Skutnik

(57) ABSTRACT

A laser device and method for treating ophthalmic diseases is enclosed. The laser device and method for treating a variety of ophthalmic diseases comprises a system for irradiating the eye with electromagnetic irradiation with a wavelength in the range of 654-681 nm from at least one high power laser diode. The optical system of the present invention being able to focus the radiation onto a spot sized of about 100 μm. The system preferably comprises a laser source and ancillary equipment to direct and regulate the radiation. The use of this wavelength range makes the present invention effective for a wide variety of ophthalmic indications. It is capable of providing photocoagulation treatments for diseases such as glaucoma, diabetic retinopathy and age-related macular degeneration.

3 Claims, 4 Drawing Sheets

401

405   403

MULTIPURPOSE DIODE LASER SYSTEM FOR OPHTHALMIC LASER TREATMENTS

REFERENCE TO A RELATED CASE

This application is a continuation-in-part of co-pending U.S. patent application Ser. No. 10/317,921 filed on Dec. 11, 2002 by Wolfgang Neuberger, Detlev Berndt, Julian Maughan, inventors, entitled "MULTIPURPOSE DIODE LASER SYSTEM FOR OPHTHALMIC LASER TREATMENTS", and incorporated by reference herein.

BACKGROUND OF THE INVENTION

1. Field of the Invention

The invention relates to ophthalmic laser treatments, particularly to devices and systems capable of performing multiple ophthalmic photocoagulation treatments.

2. Information Disclosure Statement

Ophthalmic laser treatments comprise a variety of modalities to combat different diseases or indications. Ion or dye lasers, such as Argon and Krypton lasers, have been preferred because the wavelengths they produce (488 or 514 nm for Argon, 648 nm for Krypton) are effective in various photocoagulation procedures. For example, wavelengths produced by Argon lasers are well absorbed in hemoglobin and thus are effective for coagulating hyperproliferating or leaking blood vessels that can occur in diabetic patients, among others. (see U.S. Pat. No. 5,147,349)

U.S. Pat. No. 5,295,989 describes a light cable in an apparatus for ophthalmic treatment consisting of a plurality of optical fibers. A preferred embodiment utilizes an Argon laser beam as a treatment light source.

Many of the current photocoagulators are of an inconveniently and inefficiently high cost, size and complexity. For example, conventional Krypton and Argon lasers are capable of emitting sufficient power levels for photocoagulation but are bulky, technically complex, and are inefficient "(below 0.1%) requiring up to 40 kW of three phase power and associated water cooling" to remove excess heat. (see U.S. Pat. No. 4,917,486) Thus, these setups are expensive and often require fixed installations.

The advantages of using a laser diode over other laser sources are espoused in U.S. Pat. No. 4,917,486, which describes the laser diode as having a relatively low cost (around 10-20%) compared to an Argon laser, high efficiency of around 30% providing sufficient output power with a low amount of electrical input, lack of need for water cooling and smaller size. U.S. Pat. No. 4,917,486 uses infrared light preferably at a wavelength of substantially 800 nm, which is longer than Kr or Ar wavelengths, and preferably emitted by a laser diode.

Other photocoagulation treatment methods include the use of probes for insertion into the eye prior to irradiation, the use of photosensitive substances, whose absorption spectra define the laser wavelength needed in conjunction with photodynamic therapy, and the use of two or more radiation sources simultaneously or during a single treatment to enhance treatment efficacy. Each of these alternatives require more complex procedures and equipment than the simple use of a single wavelength and thus introduce new potential problems into the treatments. They do not address the current treatment modality as does the present invention.

Generally also low energy red lasers, operating wavelengths between 600 and 700 or so nm, are often used as aiming laser beams to guide the higher power laser beam which treat the diseases. These are chosen for this function as these wavelengths are considered easy to see and not likely to induce reactions within the patient. References dealing such lasers are not directly useful to the problems solved herein and are thus excluded.

Ophthalmic treatment systems have been proposed that are capable of performing different types of treatments with a single system or device. However, to achieve different results, these systems must apply radiation at multiple wavelengths, usually through availability of multiple sources. A system that can perform multiple treatment types with a single wavelength range has not been disclosed.

Recent commercial announcements describe a new multi-laser photocoagulation laser system for treating a range of retinal diseases. The system provides a spectrum of green, yellow and red light in a single device and is claimed to be useful for age-related macular degeneration, diabetic retinopathy, diabetic macular edema and other diseases.

Likewise, U.S. Pat. No. 5,331,649 discloses a system for producing different wavelengths often needed in ophthalmic treatments. This is a system for generating a plurality of wavelengths of light in a single apparatus.

U.S. Pat. No. 5,423,798 describes a system for performing laser vitrectomy and endophotocoagulation within a single system to avoid the need to change devices between the two treatments. Two wavelengths can be applied through the same fiberoptic delivery apparatus. The first wavelength for photoablation operates at about the 2.94 micron region, and the second wavelength for photocoagulation operates at about 800 nm. The first photo-ablative laser comprises an Er:YAG crystal and the second photocoagulative laser is a semiconductor laser diode array.

U.S. Pat. No. 5,144,630 describes a wavelength conversion system for use in ophthalmic surgery. The system switches between a plurality of nonlinear crystals to allow for applying radiation with a wavelength range from ultraviolet to infrared and large enough to replace the need for the use of many traditional lasers for a variety of treatments. The ability to switch wavelengths allows one to treat a variety of conditions with one system.

The above patents illustrate the current state of the art with respect to ophthalmic, and especially photocoagulative, laser surgery. Different wavelengths are known to affect various tissue types differently, and thus different wavelengths are thought to be more effective for different treatments. The presence of multiple laser sources increases the base cost and when switching between them, potential new errors or precautions are required in their operation. It would be extremely useful, therefore to provide a laser system operating at a wavelength that is effective for a variety of photocoagulative treatments. The present invention addresses this need.

OBJECTIVES AND BRIEF SUMMARY OF THE INVENTION

It is an object of the present invention to provide a laser device and method for treating a variety of ophthalmic diseases with a single device or system.

It is another object of the present invention to provide a device and method for photocoagulation of the eye that is also capable of treating a larger number of ophthalmic diseases than any singular prior art device or method.

It is yet another object of the present invention to provide a device and method for treating ophthalmic diseases that is more convenient and economical than prior art devices and methods.

Briefly stated, the present invention describes a laser device and method for treating a variety of ophthalmic diseases. The invention comprises a system for irradiating the eye with electromagnetic irradiation with a wavelength in the range of 654-681 nm from at least one high power laser diode. The optical system of the present invention being able to focus the radiation onto a spot size of about 100 µm. The system preferably comprises a laser source and ancillary equipment to direct and regulate the radiation. The use of this wavelength range makes the present invention effective for a wide variety of ophthalmic indications. It is capable of providing photocoagulation treatments for diseases such as glaucoma, diabetic retinopathy and age-related macular degeneration. Also disclosed are laser diodes with high beam quality and slit lamp adaptors to further enhance the versatility of the system.

The above, and other objects, features and advantages of the present invention will become apparent from the following description read in conjunction with the accompanying drawings.

DETAILED DESCRIPTION OF PREFERRED EMBODIMENTS

Considering the widespread use of red wavelength lasers as safe aiming beams, it has surprisingly been found that a diode laser operating at a wavelength in the range of 654-681 nm has similar properties in ocular tissues to a number of laser wavelengths that are currently used to treat a variety of ophthalmic diseases.

The present invention contains many of the treatment properties of various wavelengths used for photocoagulation in the prior art, and has the additional advantage of being able to exhibit these properties with a single wavelength range and consequentially a single device. It can perform a number of different photocoagulation procedures that previously would have required numerous devices or a device capable of emitting various wavelengths. A medical professional can now treat these and other diseases more conveniently and inexpensively than was possible in the prior art. Because the present invention is capable of performing numerous treatments with a single wavelength, a practitioner can now avoid having to buy a number of devices to treat the range of indications that the present invention can treat with a single device.

The 668 nm laser (which emits at 668 nm+/- 20% equaling 654-681, nominally 670 nm) utilized in the present invention emits in the red part of the spectrum. The absorption characteristics of this laser are very similar to those of the 647 nm red krypton laser. Also, the 670 nm laser has transmission qualities that are very similar to those of the near infrared 810 nm diode laser and has an excellent curve that is minimally influenced by opacities and is very similar to the transmission of the near infrared 810 nm diode laser.

The 670 nm laser has been found to have excellent properties, in particular, for laser photocoagulation of the fundus. It is sufficiently absorbed by the melanin of the retina and choroid and it is relatively minimally absorbed by blood and media opacities. Therefore, retinal whitening is obtained very easily and no learning curve is needed as for the near infrared diode laser, and irradiation can accurately pass through cataracts, vitreous opacities and hemorrhages.

Figure 1:
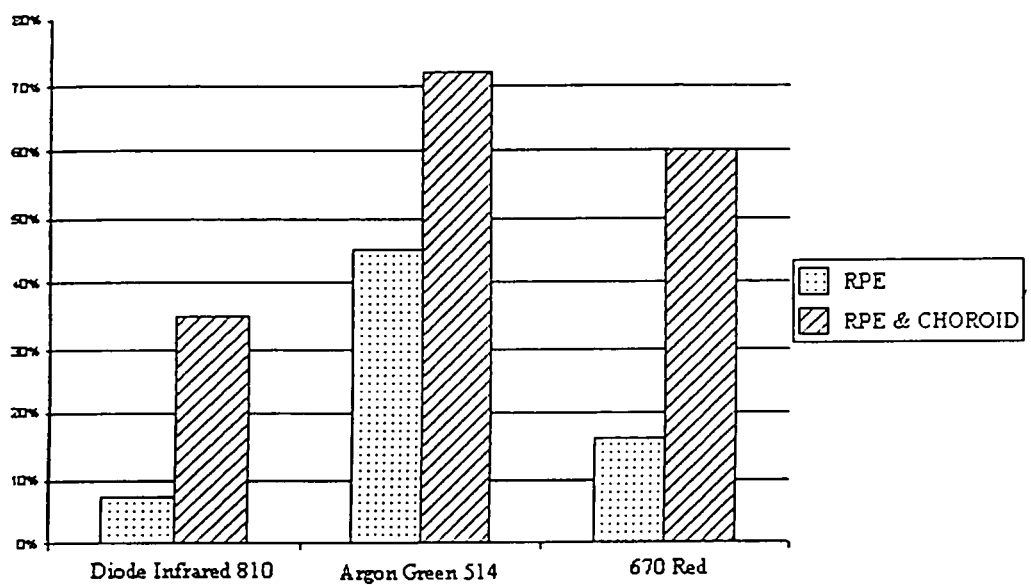
FIG. 1 illustrates by graph the absorption characteristics of various wavelengths in ocular tissue.
Figure 2:
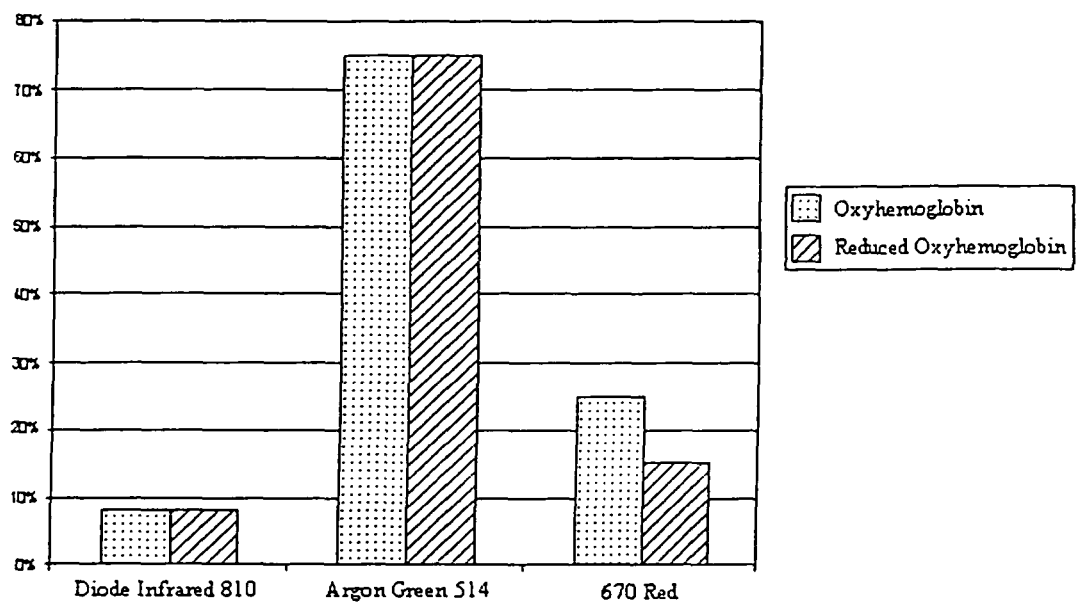
FIG. 2 illustrates by graph the absorption characteristics of various wavelengths in blood.
Figure 3:
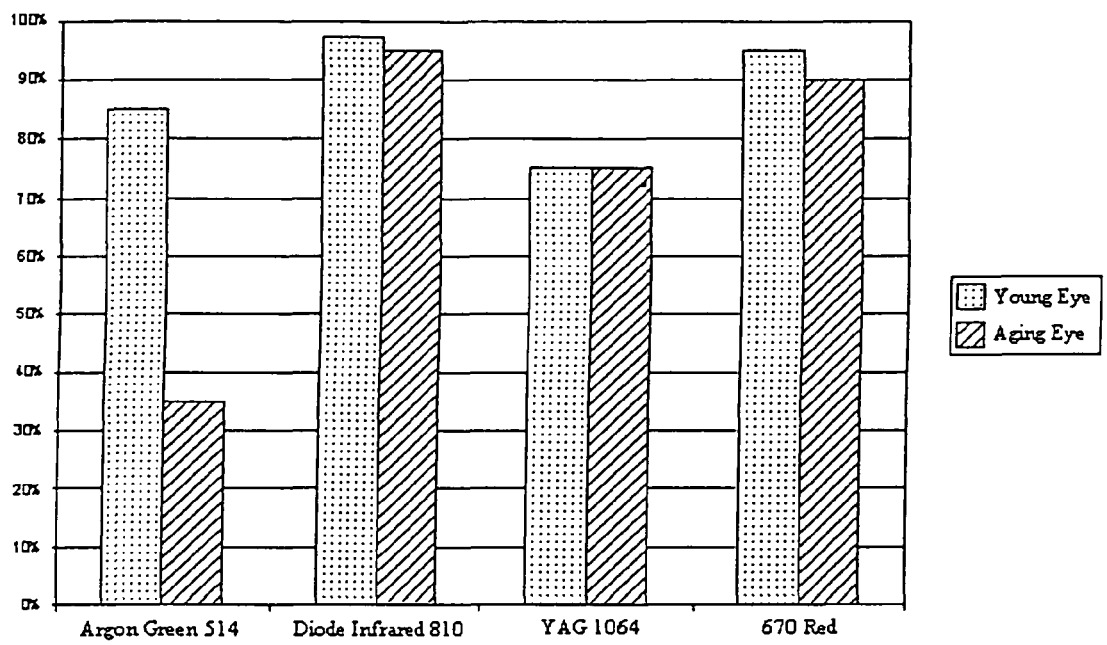
FIG. 3 illustrates by graph the transmission of various wavelengths through the ocular media.

The properties of the 670 nm diode laser, which are similar to the 810 nm diode laser are illustrated in the accompanying figures. FIG. 1 shows similar absorption properties of both the 670 nm and 810 nm lasers in the retinal pigment epithelium and choroid. FIG. 2 illustrates that, like the 810 nm laser, the 670 nm radiation of the present invention is relatively minimally absorbed in blood. Finally, FIG. 3 demonstrates similar transmission properties of the 670 nm and 810 nm lasers in the ocular media.

The present invention is useful for a number of ophthalmic indications that previously would have required different wavelengths and thus numerous laser devices or much more complex multi-laser devices. It is especially effective for those procedures that have previously utilized a Krypton, Argon, or 810 nm diode laser. The following is a brief description of many of the ophthalmic diseases that the present invention can effectively treat and the treatment modalities for which the present invention is effective. The treatment parameters using the laser device of the present invention are determined by the treating physician based upon the physician's knowledge regarding the condition being treated.

Diabetic retinopathy is characterized by retinal dot and blot hemorrhages, microaneurysms and exudates in early stages. Proliferative diabetic retinopathy, a late stage of the disease, is characterized by neovascularization and vitreous or preretinal hemorrhages. Photocoagulative treatments can successfully treat these problems. In particular, pan-retinal photocoagulation is effective for causing regression of neovascular tissues.

Glaucoma has recently been treated with a procedure known as transscleral cyclophotocoagulation, which consists of treating the ciliary body of the eye to decrease production of aqueous fluid which reduces pressure in the eye. Nd:YAG and thulium:YAG lasers have been used with this procedure. The 810 nm diode lasers have also been recognized as an effective laser for this procedure. The 810 nm diode laser is characterized by good penetration and selective absorption by the pigmented tissues of the ciliary body, which makes it an effective wavelength for this procedure. The present invention can be successfully utilized with this procedure.

The present invention can also be utilized as a photocoagulator for treating retinal vein occlusion, rhegmatogenous peripheral retinal lesions and retinal breaks and for prophylactic peripheral retinopexy prior to silicone oil removal.

The 670 nm diode laser is effective for laser treatments requiring endo-probe delivery via an incision in the eye, transcleral delivery and transpupillary delivery.

Other retinal photocoagulation treatments include transpupillary retinal photocoagulation, retinal endophotocoagulation and cyclophotocoagulation. It is generally accepted that retinal photocoagulation treatments are effective with the use of laser radiation near 800 nm.

The procedures and wavelength specifications described above have been employed in the prior art for the described indications. Because the 670 nm wavelength of the present invention features the superior penetration qualities of the near infrared wavelengths, and the absorption characteristics of red wavelengths, particularly the 647 nm wavelength, the present invention can be used to effectively treat the indications described above with a single treatment system, thus greatly reducing the complexity and expense of procuring the capability to treat such a variety of indications.

Additional benefits of the present invention, apart from its evident versatility, include power on demand (true delivery of the called-for energy upon activation), delivery of a true square pulse of energy without spikes or peaks occurring throughout the pulse cycle, and the benefits inherent in a diode system. As described above, these benefits include high efficiency and thus lower power requirements, and longer life due to reduced need for maintenance.

In a preferred embodiment, the present invention incorporates a device comprising a laser source emitting in the wavelength range of 668 nm+/− 20%, nominally 670 nm, suitable optics to focus and direct a treatment beam into a treatment area, an illuminator such as a slit lamp, and means for observing the treatment area. The source for providing the above radiation is preferably a diode laser or diode laser array.

A further object of the present invention includes new diode laser designs providing high beam quality and thus the ability to couple with very thin optical fibers (such as 50 μm core or even 20 μm core, with 0.1 N.A.), which can be coupled to slit lamp adaptors to provide superior quality beams that can have a long focal length. The ability to produce such small and high quality beams allows for even greater versatility of the present invention. Treatments for which such beams would be useful include micro photocoagulation in the region of the macula and optic disc and minimally destructive procedures in the region of the ciliary body for glaucoma treatments. A spot size of about 100 μm or less is preferred in this application. This aspect of the present invention would also be advantageous for transpupillary applications in small pupils where beam clipping of larger spot sizes can decrease power density to ineffective levels. A smaller spot diameter, such as noted above, would also be desirable in the treatment of Retinopathy of Prematurity (RoP), which is an increasing condition owing to improved mortality rates of premature babies and if left untreated always leads to blindness.

In a preferred embodiment, "bow-tie" or trapezoidal diode lasers emitting near single mode radiation with a wavelength of 670 nm are used to produce a high quality beam. These diode lasers have a flared, highly diverging region that is in the shape of a trapezoid or a "bow-tie". The beam is then coupled to an oligimode optical fiber with suitable optics such as step-mirrors so as to preserve beam quality during coupling. For delivery of the treatment radiation to the eye, the optical fiber is coupled to a slit lamp adaptor. The slit lamp adaptor determines the spot sizes and includes attenuation means that effectively attenuate the power received from the laser source. Thus a monotonic relationship between the spot diameter and the laser power administered is easily achieved. Preferably the attenuation means is chosen such that the intensity of the beam is independent of the spot size. In a preferred embodiment, the attenuation means is in the form of an iris whose aperture is varied in accordance with the movement of a selection ring to select a beam spot size. In another embodiment, the attenuation means is an attenuator disc rotated in accordance with selection ring at a suitable point in the optical path. In this manner the laser unit itself can be simplified to only produce a constant power output, and if this is desirable, only the time of irradiation needs to be varied to achieve different treatment dosages. Other embodiments may include adaptors to indirect opthalmoscopes or may include a slit lamp that has already included in its structure the spot size selection mechanism as described above.

In one preferred embodiment, the diode lasers are mounted on the slit lamp and coupled thereto with optical fibers. This eliminates the need for a separate laser unit connected via optical fibers to the so-called slit lamp adaptor mounted on the slit lamp. By reducing the distance, eliminating optical components, reducing connections, results in better beam quality with the new system.

Figure 4:
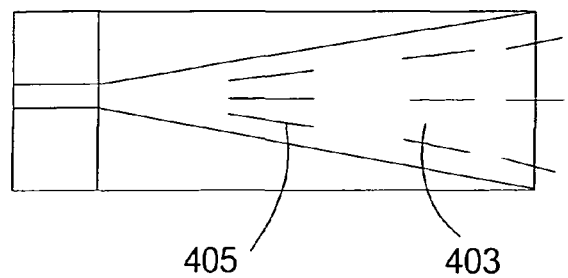
FIG. 4 illustrates a preferred high power diode laser.

FIG. 4 illustrates a preferred embodiment of a treatment system according to the present invention. The system consists of diode laser 401 emitting 670 nm wavelength radiation having tapered gain region 403 for producing a high quality beam from radiation 405.

Figure 5:
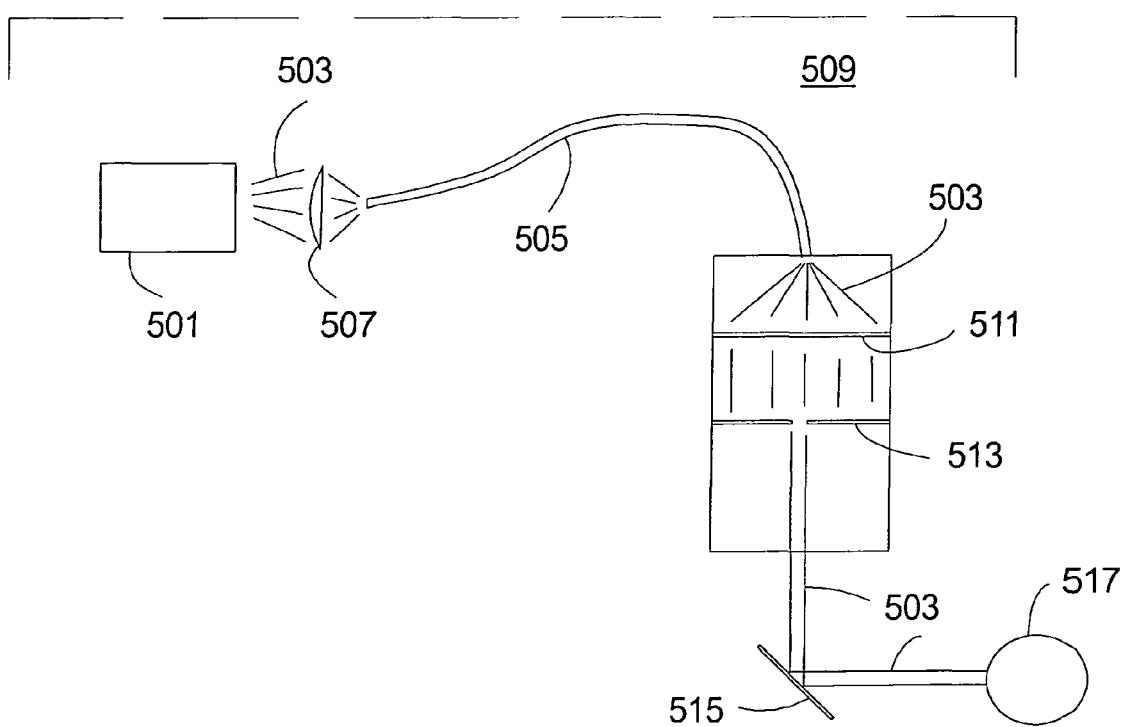
FIG. 5 illustrates a preferred embodiment of a treatment device utilizing a slit-lamp adaptor connected to the laser diodes by an optical fiber.

As shown in FIG. 5, a slit lamp adaptor 520 shows radiation 503 emitted from at least one high power diode laser 501 is coupled into low-mode optical fiber 505 by means of focusing optics 507. Optical fiber 505 delivers radiation 503 to slit-lamp 509 for delivery of a beam of radiation 503, with a spot size that is controllable without changing power density. It is preferred that the spot size be about 100 μm or less. Slit-lamp 509 consists of collimating optics 511 for collimating beam 503, adjustable iris 513 for adjusting beam spot size, and mirror 515 to direct beam 503 to eye 517. Laser diodes 501 being mounted onto slit-lamp adaptor 520 connect diodes 501 to slit lamp 509 with optical fiber 505.

A laser system of the present invention using the laser diodes outputting in a range from about 650 to about 680 μm with the above optical system is able to output over 900 mW of radiation to a spot size of less than or about 100 μm.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. An ophthalmic laser treatment device for direct treatment of an eye's fundus, for a variety of conditions comprising:
   a high power laser diode radiation source emitting radiation having a wavelength of 668 nm+/−2.0%, providing about 1 W per single laser diode;
   a slit lamp adaptor including an attenuation component for outputting a laser beam having a spot size at a treatment site in said eye's fundus of 100 μm or less, to direct and control said radiation to a treatment area in an eye, wherein said spot size is variably controllable without changing power density at a treatment site within said eye's fundus; and
   an optical fiber coupled to said high power laser diode radiation source and delivering radiation from said high power laser diode radiation source to said slit lamp adaptor, wherein said optical fiber is an oligimode fiber having a core diameter not greater than 50 μm and a Numerical Aperture of about 0.1; wherein said laser diode radiation source emits near single mode radiation and has a light diverging gain region selected from a group consisting of a trapezoidal shaped region and a "bow-tie" shaped region.

2. A method for ophthalmic laser treatments, comprising the steps of:
   predetermining treatment parameters;
   directing radiation having a wavelength of 668 nm+/−2.0% from a laser diode radiation source to an area of treatment of an eye using said determined treatment parameters, said laser diode radiation source emitting near single mode radiation and having a light diverging gain region selected from a group consisting of a trapezoidal shaped region and a "bow-tie" shaped region and comprising at least one high power laser diode, providing about 1 W per single laser diode; delivering radiation from said radiation source to a slit lamp adaptor, the radiation being delivered to said treatment area through the slit lamp adaptor including an attenuation component, by an optical fiber coupled to said laser diode radiation source, wherein said optical fiber is an oligi-mode fiber having a core diameter not greater than 50 µm and a Numerical Aperture of about 0.1, said radiation being output to a spot of about 100 µm or less in the area of treatment; and irradiating said treatment area of said eye, wherein power density on said treatment area is constant though spot size is controllably variable, with said radiation resulting in said treatment.

3. The method according to claim 2, wherein said step of directing said radiation is accomplished by providing entry of said radiation to said treatment area transsclerally or transpupillarily.

* * * * *